(12) United States Patent
Norton et al.

(10) Patent No.: US 11,147,586 B2
(45) Date of Patent: Oct. 19, 2021

(54) ACCESS DEVICE HAVING MODULAR INSERTS AND SUPPORTING ACCESSORIES USED IN MINIMALLY INVASIVE SURGICAL PROCEDURES

(71) Applicant: Axcess Instruments Inc., Tyler, TX (US)

(72) Inventors: Michael J. Norton, Tyler, TX (US); Noel D. Ischy, Tyler, TX (US)

(73) Assignee: Axcess Instruments Inc., Tyler, TX (US)

( * ) Notice: Subject to any disclaimer, the term of this patent is extended or adjusted under 35 U.S.C. 154(b) by 0 days.

(21) Appl. No.: 16/897,870

(22) Filed: Jun. 10, 2020

(65) Prior Publication Data

US 2020/0297379 A1     Sep. 24, 2020

Related U.S. Application Data

(60) Division of application No. 15/786,265, filed on Oct. 17, 2017, now Pat. No. 10,687,847, which is a
(Continued)

(51) Int. Cl.
    *A61B 17/02*      (2006.01)
    *A61M 39/02*      (2006.01)
    (Continued)

(52) U.S. Cl.
CPC ...... *A61B 17/3423* (2013.01); *A61B 17/0218* (2013.01); *A61B 17/3421* (2013.01); *A61B 90/30* (2016.02); *A61B 90/361* (2016.02); *A61M 39/02* (2013.01); *A61M 39/0247* (2013.01); *A61M 39/06* (2013.01); *A61B 17/3462* (2013.01); *A61B 2017/00283* (2013.01); *A61B 2017/00477* (2013.01); *A61B 2017/3445* (2013.01); *A61B 2017/3466* (2013.01);
(Continued)

(58) Field of Classification Search
CPC .................................................. A61B 17/3423
See application file for complete search history.

(56) References Cited

U.S. PATENT DOCUMENTS

| 6,436,086 B1 | 8/2002 | Newby et al. |
| 6,551,270 B1 | 4/2003 | Bimbo et al. |
(Continued)

FOREIGN PATENT DOCUMENTS

WO      2014192788 A1     12/2014

*Primary Examiner* — Tessa M Matthews
(74) *Attorney, Agent, or Firm* — Locke Lord LLP; Scott D. Wofsy

(57) ABSTRACT

A percutaneous access device for use in minimally invasive surgery includes an elongated body having a proximal portion and an opposing distal portion. The proximal portion has a proximal bore extending therethrough and the distal portion has a distal bore extending therethrough. The distal portion of the body is hingedly connected to the proximal portion in a first percutaneous access position and a second anchoring position. In the first percutaneous access position the distal and proximal bores are linearly aligned when a surgical instrument is inserted into both the proximal and distal bores. In the second anchoring position the distal bore is angularly displaced from the proximal bore when the surgical instrument is removed from the distal bore.

13 Claims, 11 Drawing Sheets

Related U.S. Application Data continuation-in-part of application No. 15/098,301, filed on Apr. 13, 2016, now Pat. No. 10,278,730.

(60) Provisional application No. 62/526,782, filed on Jun. 29, 2017, provisional application No. 62/467,593, filed on Mar. 6, 2017, provisional application No. 62/467,596, filed on Mar. 6, 2017, provisional application No. 62/429,439, filed on Dec. 2, 2016, provisional application No. 62/409,104, filed on Oct. 17, 2016, provisional application No. 62/277,427, filed on Jan. 11, 2016, provisional application No. 62/238,245, filed on Oct. 7, 2015, provisional application No. 62/192,872, filed on Jul. 15, 2015.

(51) Int. Cl.
*A61B 17/00* (2006.01)
*A61B 17/34* (2006.01)
*A61M 39/06* (2006.01)
*A61B 90/30* (2016.01)
*A61B 90/00* (2016.01)

(52) U.S. Cl.
CPC ............... *A61B 2017/3482* (2013.01); *A61B 2017/3484* (2013.01); *A61M 2039/0255* (2013.01); *A61M 2039/0261* (2013.01); *A61M 2039/0279* (2013.01)

(56) References Cited

U.S. PATENT DOCUMENTS

| | | |
|---|---|---|
| 6,811,546 B1 | 11/2004 | Callas et al. |
| 8,016,796 B2 | 9/2011 | Simas, Jr. et al. |
| 8,795,289 B2 | 8/2014 | Fowler et al. |
| 9,011,319 B2 | 4/2015 | Norton et al. |
| 9,017,251 B2 | 4/2015 | Stopek |
| 2001/0004970 A1 | 6/2001 | Hollister et al. |
| 2005/0049560 A1 | 3/2005 | Hauri |
| 2005/0057684 A1* | 3/2005 | Tamakoshi ............ A61B 90/36 348/375 |
| 2006/0247500 A1 | 11/2006 | Voegele et al. |
| 2007/0265566 A1 | 11/2007 | Simpson et al. |
| 2008/0058851 A1* | 3/2008 | Edelstein ............ A61B 17/3415 606/185 |
| 2009/0012477 A1 | 1/2009 | Norton et al. |
| 2009/0036745 A1 | 2/2009 | Bonadio et al. |
| 2010/0133886 A1* | 6/2010 | Gi ............................. B60N 2/12 297/341 |
| 2010/0204548 A1 | 8/2010 | Bonadio et al. |
| 2010/0217087 A1 | 8/2010 | Bonadio et al. |
| 2010/0240958 A1 | 9/2010 | Abrams et al. |
| 2010/0249516 A1 | 9/2010 | Shelton, IV et al. |
| 2010/0324375 A1 | 12/2010 | Piskun |
| 2011/0264091 A1 | 10/2011 | Koppleman et al. |
| 2012/0149987 A1 | 6/2012 | Richard et al. |
| 2012/0232339 A1 | 9/2012 | Csiky |
| 2013/0137932 A1* | 5/2013 | Piech ........................ A61B 1/32 600/204 |
| 2013/0274559 A1 | 10/2013 | Fowler et al. |
| 2014/0074135 A1 | 3/2014 | Hart et al. |
| 2014/0094655 A1 | 4/2014 | Newman |
| 2014/0288377 A1 | 9/2014 | Worrel |
| 2014/0309495 A1* | 10/2014 | Kirma ..................... A61B 1/053 600/109 |
| 2015/0099930 A1 | 4/2015 | Knapp |
| 2015/0141755 A1* | 5/2015 | Tesar ..................... A61B 34/20 600/111 |
| 2015/0297299 A1 | 10/2015 | Yeung et al. |
| 2016/0022146 A1* | 1/2016 | Piron ..................... A61B 5/0035 600/411 |
| 2016/0081714 A1 | 3/2016 | Kobayashi et al. |
| 2016/0089181 A1* | 3/2016 | Johnson ............ A61B 17/0218 600/424 |
| 2016/0302826 A1* | 10/2016 | Prati ................. A61B 17/0218 |
| 2017/0056625 A1 | 3/2017 | Pillai |
| 2018/0125471 A1* | 5/2018 | Schaefer ............ A61B 17/3421 |
| 2018/0125603 A1* | 5/2018 | Cantor ............... A61B 17/3423 |
| 2019/0008603 A1 | 1/2019 | Hansen et al. |

* cited by examiner

ACCESS DEVICE HAVING MODULAR INSERTS AND SUPPORTING ACCESSORIES USED IN MINIMALLY INVASIVE SURGICAL PROCEDURES

CROSS-REFERENCE TO RELATED APPLICATIONS

This application is a divisional of U.S. patent application Ser. No. 15/786,265, filed Oct. 17, 2017, which application is a continuation-in-part of U.S. patent application Ser. No. 15/098,301 filed on Apr. 13, 2016. This application claims the benefit of and priority to U.S. Provisional Patent Application No. 62/409,104, filed on Oct. 17, 2016, U.S. Provisional Patent Application No. 62/429,439, filed on Dec. 2, 2016, U.S. Provisional Patent Application No. 62/467,593, filed on Mar. 6, 2017, U.S. Provisional Patent Application No. 62/467,596, filed on Mar. 6, 2017, and U.S. Provisional Patent Application No. 62/526,782, filed on Jun. 29, 2017, the disclosures of which are hereby incorporated by reference herein in their entireties.

U.S. application Ser. No. 15/098,301 claims the benefit of and priority to U.S. Provisional Patent Application No. 62/192,872, filed Jul. 15, 2015, U.S. Provisional Patent Application No. 62/238,245, filed Oct. 7, 2015, and U.S. Provisional Patent Application No. 62/277,427, filed Jan. 11, 2016, the disclosures of which are hereby incorporated by reference herein in their entireties.

BACKGROUND OF THE INVENTION

1. Field of the Invention

The subject invention is directed to surgery, and more particularly, to an anchored access port having an attachment to support accessories, such as imaging and lighting devices, used in minimally invasive surgical procedures performed within the abdominal cavity of a patient, including, but not limited to, laparoscopic surgical procedures.

2. Description of Related Art

Laparoscopic or "minimally invasive" surgical techniques are becoming commonplace in the performance of procedures such as cholecystectomies, appendectomies, hernia repair and nephrectomies. Benefits of such procedures include reduced trauma to the patient, reduced opportunity for infection, and decreased recovery time. Such procedures within the abdominal (peritoneal) cavity are typically performed through a device known as a trocar or cannula, which facilitates the introduction of laparoscopic instruments into the abdominal cavity of a patient.

Additionally, such procedures commonly involve filling or "insufflating" the abdominal (peritoneal) cavity with a pressurized gas such as carbon dioxide, to create what is referred to as a pneumoperitoneum. The insufflation can be carried out by a surgical access device (sometimes referred to as a "cannula" or "trocar") equipped to deliver insufflation gas, or by a separate insufflation device, such as an insufflation (veress) needle. Introduction of surgical instruments into the pneumoperitoneum without a substantial loss of insufflation gas is desirable, in order to maintain the pneumoperitoneum.

During laparoscopic procedures, a surgeon makes three to four small incisions, between 12 mm and 25 mm in length depending upon the device type, usually no larger than about twelve millimeters each, which are typically made with the surgical access devices themselves, often using a separate inserter or obturator placed therein. Following insertion, the inserter is removed, and the trocar allows access for instruments to be inserted into the abdominal cavity. Typical trocars often provide means to insufflate the abdominal cavity, so that the surgeon has an open interior space in which to work.

The trocar must provide a means to maintain a desired pressure within the cavity by sealing between the trocar and the surgical instrument being used, while still allowing at least a minimum freedom of movement of the surgical instruments. Such instruments can include, for example, scissors, linear staplers, grasping instruments, and occluding instruments, cauterizing units, cameras, light sources and other surgical instruments. Sealing elements or mechanisms are typically provided on trocars to prevent the escape of insufflation gas. Sealing elements or mechanisms typically include a duckbill-type valve made of a relatively pliable material, to seal around an outer surface of surgical instruments passing through the trocar.

Anchoring means must also be provided for securing the trocar or cannula to a patient's abdominal wall during a procedure to prevent the access device from inadvertently withdrawing from the incision through which it has been extended. This is typically accomplished using sutures that are passed through eyelets or similar tie-down features provided on the housing of the trocar or cannula. However, the sutures that are used in this manner can often cause increased trauma to the patient, add complexity to the surgical procedure and create obstructions near the surgical site making it more difficult for the surgeon to operate.

In many of these surgical procedures, several access ports are required, each one dimensioned to receive a particular surgical instrument for use at the surgical site. One of the access ports is typically configured to receive the endoscopic camera that is used for viewing the abdominal cavity and enabling display of the cavity and the manipulation of the instrumentation and tissue within the body cavity on a video monitor viewed by the surgeon.

Percutaneous access devices allow for smaller instruments to be placed into an operative field or space through smaller incisions than open surgery.

It would be beneficial to have an anchoring device inside the operative space during surgeries or interventions to decrease the incidence of device withdrawal until the procedure/operation has been completed. With an anchor in the operative space, it is not necessary to have resistance modifications on the tube such as ribs, screws or textured surfaces which add resistance not only to removal but also to insertion. It would be beneficial for the device insertion to be easier by decreasing the friction coefficient of the percutaneous device and instead relying on a multifunctional boot tip anchor to prevent withdrawal.

Therefore, there is a need in the art for a surgical access device that overcomes many of the disadvantages of prior art surgical access devices, including, among others, those associated with the use of anchoring sutures to secure the access device in place during a surgical procedure. It would also be advantageous to reduce the number of access ports in the abdominal cavity while maintaining the same instrumentation and maneuverability of the instruments within the body cavity. More particularly, it would be advantageous to incorporate certain accessory devices, such as a camera, laser or light source into the access device itself, either integrally or by way of a modular attachment, in order to reduce the number of access ports employed during a surgical procedure.

SUMMARY OF THE INVENTION

The subject invention is directed to a new and useful surgical percutaneous access device and an access port for use in minimally invasive surgical procedures, such as, for example, laparoscopic surgical procedures performed within a patient's abdominal cavity that overcomes the disadvantages associated with prior art surgical access devices, including the use of anchoring sutures to secure the device in place during a procedure.

In an embodiment of the subject invention a percutaneous access device for use in minimally invasive surgery is disclosed. The percutaneous access device includes an elongated body having a proximal portion and an opposing distal portion. The proximal portion has a proximal bore extending therethrough and the distal portion has a distal bore extending therethrough. The distal portion of the body is hingedly connected to the proximal portion in a first percutaneous access position and a second anchoring position. In the first percutaneous access position the distal and proximal bores are linearly aligned when a surgical instrument is inserted into both the proximal and distal bores. In the second anchoring position the distal bore is angularly displaced from the proximal bore when the surgical instrument is removed from the distal bore.

The distal portion of the body can include a shape memory material configured to automatically hinge the distal portion from the first position to the second position when the at least one surgical instrument is slidably removed from the distal bore.

When the distal portion is in the second position, the proximal bore can include an open end configured to allow the at least one surgical instrument access to the interior of the patient's body. When the distal portion is in the first position the distal bore can be sealed by a distal tip. When the distal portion is in the second position, the distal portion can be approximately ninety degrees with the body.

The percutaneous access device can include an instrument channel along a perimeter of the body from the proximal portion to the distal portion configured to accept a guidewire therethrough. The proximal portion of the body can include an O-ring seal configured to slideably engage with an outer surface of the body. The O-ring seal can be configured to provide a barrier to advancement of the device through the patient's body when the seal reaches the skin surface. The O-ring seal can further include a sensor configured to measure the longitudinal advancement of the device within the patient's body. The distal portion of the percutaneous access device can be adapted and configured to support one or more accessories used during a surgical procedure. The accessories associated with the distal portion can be selected from the group consisting of an optical imaging device, a camera device, a scope, a video device, a light source, a lighting device, a laser device, a measuring device, a laser measuring device, a signal transmitting device, a signal receiving device, a signal processing device, a memory storage device, a wiring device, a servo driven device, a gear device, an irrigation device, and/or a suction device. A power source can be electronically coupled to a cable extending along the body to the distal portion configured to provide power to the one more accessories.

In another embodiment, an access port for use in minimally invasive surgical procedure performed within a patient's abdominal cavity is shown and described. The access port includes a body defining a bore configured to guide at least one surgical instrument into a patient's abdominal cavity. A first anchoring portion is integrally formed with the body. An imaging system is coupled to the body. The imaging system is integrated with a local positioning system and an operative positioning system to communicate three dimensional positions and views of components utilized in during the surgical procedure.

The imaging system can be attached to the access port by a removable auxiliary module. The removable auxiliary module can be integrally coupled to the body of the access port which contains instruments, mechanical channels, control servos power cables, connectors and computer equipment to operate and communicate with a removable instrument module and modular anchor tip devices.

The body can include a coupling device configured to allow the body to be controlled independently of other functions performed through the bore or from the auxiliary module.

The imaging system can include one or more cameras remotely controlled, the one or more cameras configured to continuously view a three dimensional grid surrounding the access port. The three dimensional grid viewed by the one or more cameras can be translated to create a holographic image of the operative field. The imaging system can further include imaging devices and position sensors located in one or more positions in the operating room. The three dimensional grid can be configured to be recorded into a central data storage supporting artificial intelligence to produce independent camera movement based on position sensor utilization positions and the corresponding camera position. The optical system can be activated when a surgical instrument is placed through the access port.

In an embodiment, an access port for use in minimally invasive surgical procedure performed within a patient's abdominal cavity includes a body defining a bore configured to guide at least one surgical instrument into a patient's abdominal cavity. At least one anchoring portion integrally formed with the body wherein the anchoring portion includes at least one imaging device.

The anchoring portion can include a transparent shield configured to protect the first anchoring portion during and after insertion of the access port within the patient's abdominal cavity. The transparent shield includes a multi-layer structure monolithically formed with the anchoring portion.

In certain embodiments a kit for use in minimally invasive surgical procedures performed within a patient's abdominal cavity is shown and described. An access port has a body defining a bore configured to guide at least one surgical instrument into a patient's abdominal cavity and a first anchoring portion integrally formed with the body. A second anchoring portion is configured for detachable coupling with the first anchoring portion and articulating movement within the abdominal cavity relative to the body.

The second anchoring portion can include a fixed segment and at least one mobile segment. The at least one mobile segment can be configured for operative association with a control device outside of the patient's abdominal cavity. The second anchoring portion can include one or more position sensors configured to electronically communicate with a local positioning system.

A port extension adapter can have a proximal end defining an inlet, and a distal end configured for detachable engagement with the body of the access port, the distal end of the port extension adapter defining an outlet configured to fluidly couple to a proximal end of the bore of the access port.

In another certain embodiment a kit for use in minimally invasive surgical procedures performed within a patient's abdominal cavity includes a body defining a solid structure and a first anchoring portion integrally formed with the body. A second anchoring portion is configured for detachable coupling with the first anchoring portion and articulating movement within the abdominal cavity relative to the body.

These and other features of the surgical access port of the subject invention and the manner in which both are manufactured and employed will become more readily apparent to those having ordinary skill in the art from the following enabling description of the preferred embodiments of the subject invention taken in conjunction with the several drawings described below.

BRIEF DESCRIPTION OF THE DRAWINGS

So that those skilled in the art to which the surgical access port of the subject invention appertains will readily understand how to make and use the subject invention without undue experimentation, preferred embodiments thereof will be described in detail herein below with reference to certain figures, wherein.

DETAILED DESCRIPTION OF PREFERRED EMBODIMENTS

Figure 1:
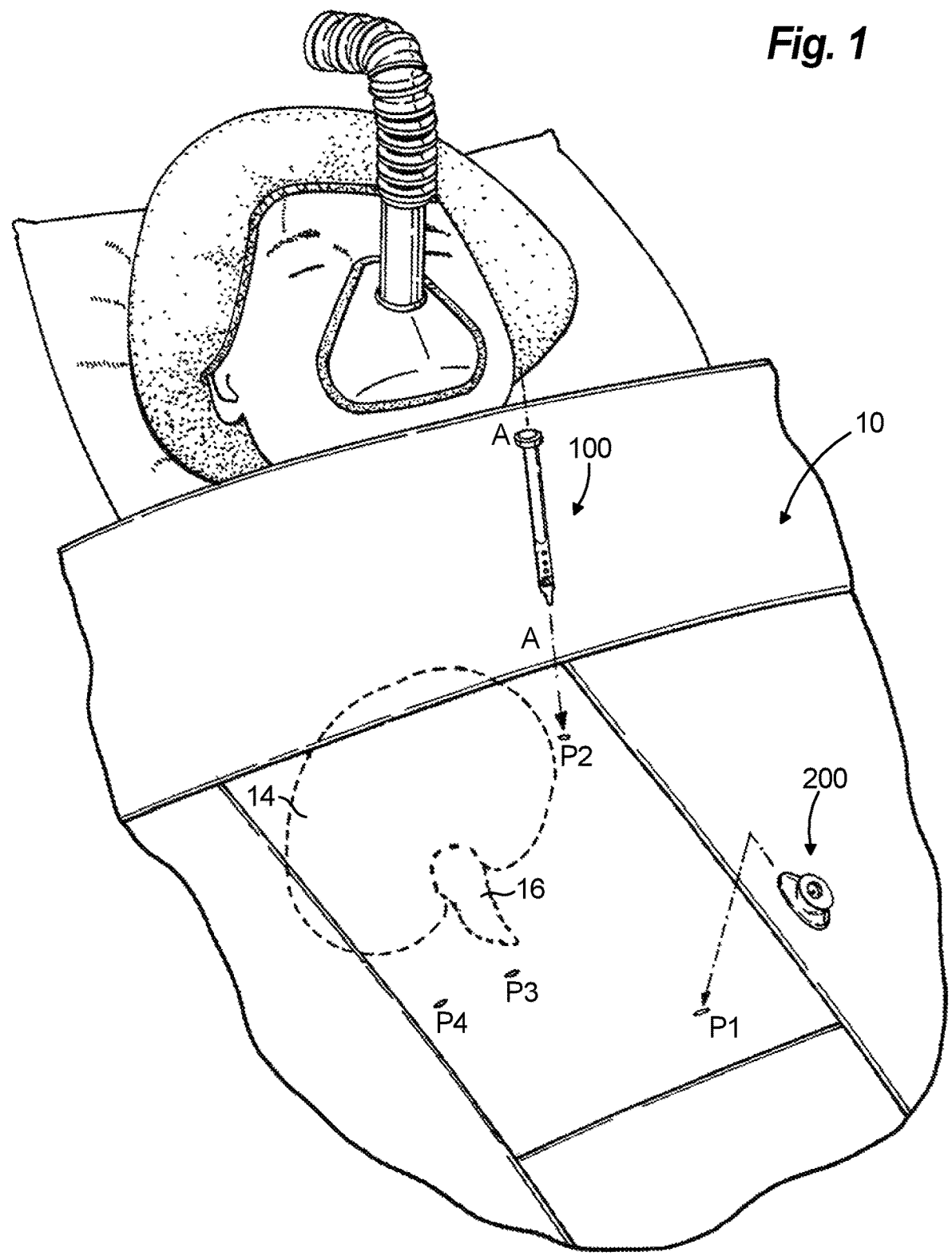
FIG. 1 is a perspective view of a percutaneous access device of the subject invention inserted into an incision in an abdominal wall of a patient, an anchored access port is simultaneously inserted near the percutaneous access device for a minimally invasive surgical procedure.

Referring now to the drawings wherein like reference numerals identify similar structural features or aspects of the subject invention, there is illustrated in FIG. 1 a new and useful surgical percutaneous access device 100 and an access port 200 for use in minimally invasive surgical procedures, such as, for example, laparoscopic surgical procedures performed within a patient's abdominal cavity.

Surgical access port 200 provides certain improvements over the advantageous surgical access port devices disclosed in commonly assigned U.S. Pat. No. 9,011,319 to Norton et al., U.S. Patent Application Publication No. 2007/0208312 to Norton et al., U.S. Patent Application Publication No. 2015/0216562 to Norton et al., and U.S. Provisional Patent Application No. 60/779,136 to Norton, the disclosures of which are hereby incorporated by reference herein in their entireties. Surgical access port 200 also provides certain improvements over advantageous surgical access port devices disclosed in related International Patent Publication No. WO 2009/128811 to Norton et al., U.S. Provisional Patent Application No. 61/124,066 to Norton et al., U.S. Provisional Patent Application No. 60/965,404 to Norton et al., and U.S. Provisional Patent Application No. 60/961,802 to Norton et al., the disclosures of which are hereby incorporated by reference herein in their entireties. These improvements relate at least in part to the increased modularity of the access port, adapting it for use in a variety of different surgical procedures, as will be discussed in more detail herein below.

Figure 2:
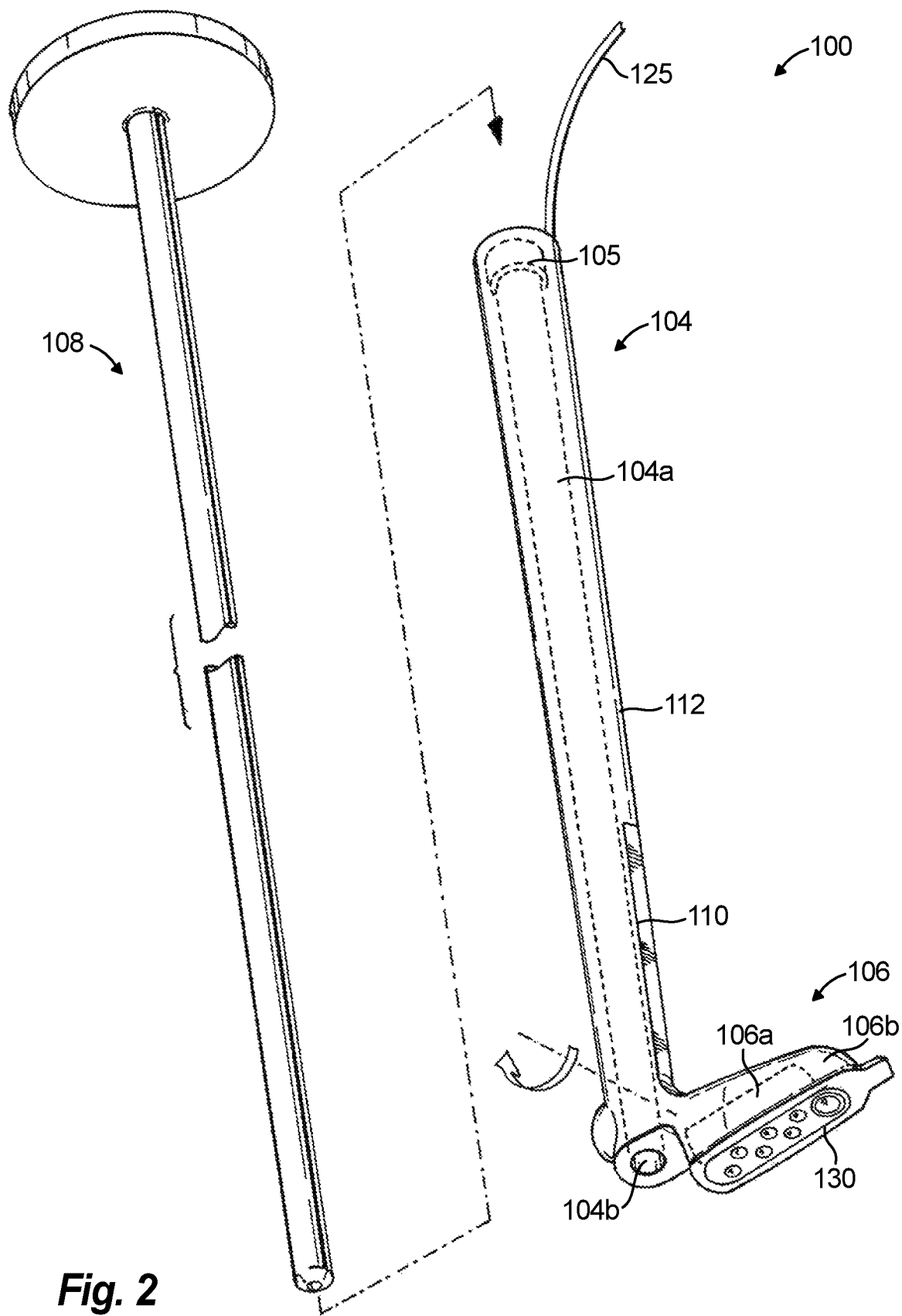
FIG. 2 is an exploded perspective view of the percutaneous access device of FIG. 1, showing a distal portion angularly displaced from a proximal portion.

Referring now to FIG. 1, an exemplary minimally invasive laparoscopic procedure 10 is shown with four incisions, P1, P2, P3, P4 within a patient's abdominal wall 12, surrounding the patient's liver and gall bladder. As shown, each incision accepts an anchoring device for example a percutaneous access device 100 or an access port 200. With reference to FIGS. 1 and 2, the percutaneous access device is shown in more detail. The percutaneous access device 100 includes an elongated body 102 with a proximal portion 104 and an opposing distal portion 106. The body 102 narrowly tapers from the proximal portion 104 to the distal portion 106 such that a diameter of the distal portion 106 is smaller than a diameter of the proximal portion 104.

The proximal portion 104 has a proximal bore 104a extending therethrough. Similarly, the distal portion 106 has a distal bore 106a extending therethrough. The proximal and distal bores 104a, 106a are designed and configured to allow a surgical instrument 108, for example, an obturator through the body 102 of the device 100. The proximal portion 104 may include a seal 105 of appropriate size for the diameter of the proximal portion 104 surrounding the surgical instrument 108.

With continued referenced to FIG. 2, the distal portion 106 hingedly connects to the proximal portion 104. In other words, the distal portion 106 hinges between a first percutaneous access position (shown in FIG. 1) and a second anchoring position (shown in FIG. 2). In the first percutaneous access position the proximal and distal bores 104a, 106a are linearly aligned along an axis A of the body 102 when the surgical instrument 108 is inserted into both the proximal and distal bores 104a, 106a. In the second anchoring position, the distal bore 106a is angularly displaced from the proximal bore 104 when the surgical instrument 108 is removed from the distal bore 106a.

In order to hinge between the first percutaneous access position and the second anchoring position, a shape memory material 110 is positioned along an outer surface 112 of the elongated body 102. As shown in FIG. 2, the shape memory material 110 can extend along a portion of the proximal and distal portions 104, 106, however any similar configuration that allows the distal portion 106 to be angularly displaced is contemplated.

The shape memory material 110 allows the distal portion 106 to be angularly displaced from the proximal portion 104 once the surgical instrument 108 is removed from the distal bore 106a. Preferably, the shape memory material 110 is flexible enough to assume a straight position and strong enough to maintain the hinged position during the surgical procedure. It is envisioned that the shape memory material 110 is mechanically structured into the elongated body 102 or mechanically attached to the elongated body 102, as appropriate.

Figure 4:
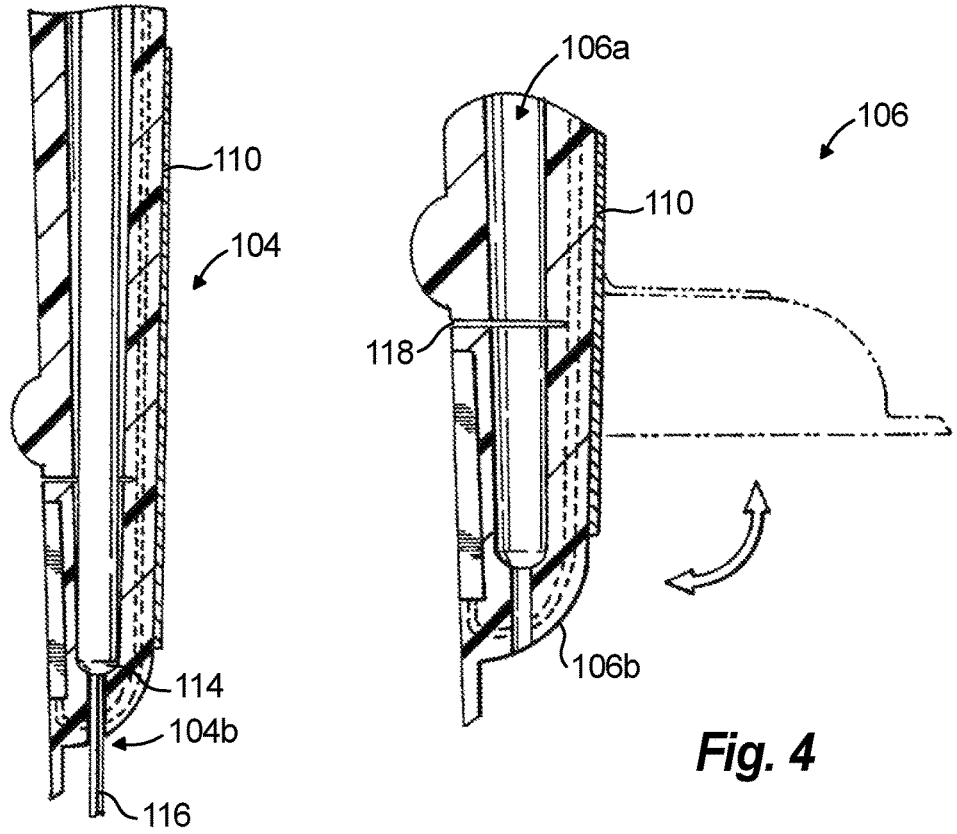
FIG. 4 is a cross-sectional view of the distal portion of the percutaneous access device.

As best seen in FIG. 4, a horizontal cut or separation 118 extends inwardly from the outer surface of the body 102 which allows the distal portion 106 to be angularly displaced. As best seen in FIG. 2, the distal portion 106 includes a distal tip 106b which seals the percutaneous device 100. During a surgical procedure, the surgical instrument 108 is inserted into the proximal and distal bores 104a, 106a thereby establishing the percutaneous device 100 in the first percutaneous access position. The percutaneous access device 100 may then be inserted into one incision, for example P2.

Once the surgeon has inserted the percutaneous access device 100 sufficiently into the patient's abdominal cavity, the surgeon slideably releases the distal portion 106 by pulling the surgical instrument 108 proximally. In doing so, the distal portion 106 automatically hinges to the second anchoring position due to the shape memory material 110. In general, the distal portion 106 is in a ninety degree angle with the proximal portion 104 when in the anchoring position. The surgeon can then slide the surgical instrument 108 again distally towards and through an open end 104b of the proximal bore 104a (best shown in FIG. 5) to access the interior of the abdominal cavity.

Figure 3:
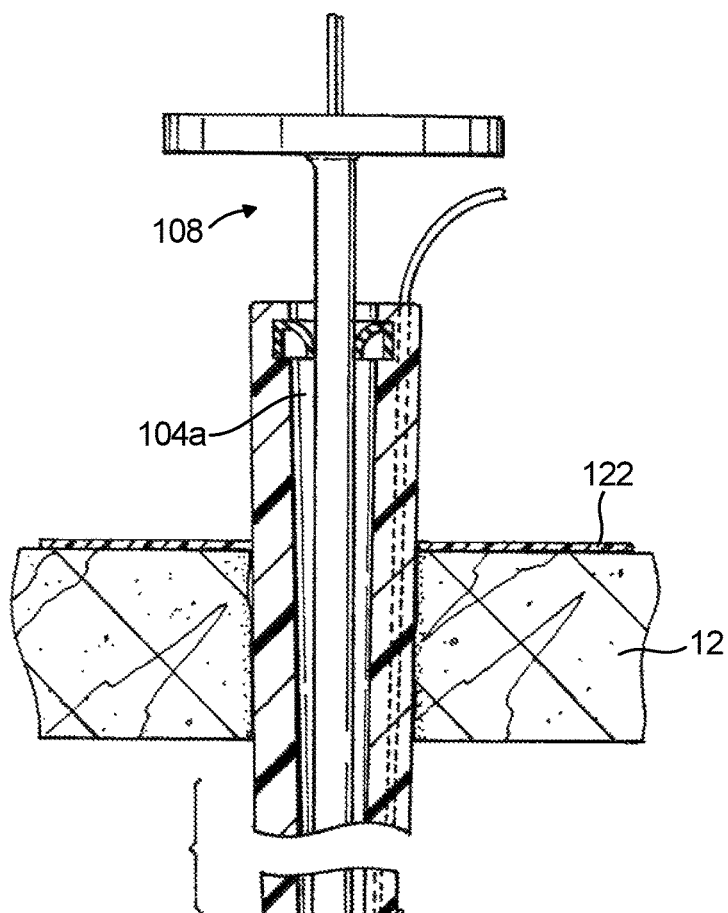
FIG. 3 is a cross-sectional view of the proximal portion of the percutaneous access device.

With reference to FIGS. 3 and 4, the percutaneous access device 100 can also include an instrument channel 114 to accept a guidewire 116 therethrough. The guidewire 116 can allow access to the operative space by visual or other forms of imaging/location identification. This would be useful in accessing the calyx of the kidney for percutaneous treatment of kidney stones or an abscess cavity.

The percutaneous access device 100 may further include an O-ring seal 122 configured to provide a barrier to advancement of the device through the patient's body when the seal reaches the skin surface. The O-ring seal 122 is positioned around the body 102 of the percutaneous access device 100. The seal 122 may be of hardened material or of elastomeric material. It is envisioned that an inner diameter of the O-ring seal 122 may be one of any diameter to engage the body 102 of the access device 100. The inner diameter may in a central position or any eccentric positioning as needed to adjust for form and function. An outer diameter of the O-ring is not limited to the shape of the device. For example, the shape of the outer diameter may be teardrop, oblong or any geometric shape. Alternative interior diameters may be of any shape that will accommodate any external diameter or shape of the percutaneous access device 100.

The O-ring seal 122 is designed to slideably engage with the outer surface 112 of the device 100. The percutaneous access device 100 has a variable enlarging diameter from the distal portion 106 to the proximal portion 104. As the O-ring seal 122 is moved proximally, the O-ring seal 122 will reach a longitudinal position on the body 102 of the device 100 where the seal 122 can no longer advance. In this manner, the O-ring seal further provides longitudinal stability to the device 100 which is important in obtaining precision measurements from the device 100 or sending and/or receiving precision measurements.

In certain embodiments, the O-ring seal 122 may have embedded or attached measuring devices, signal devices, location identifiers, GPS or Bluetooth or other communication devices that allow the O-ring to integrate into a local or remote system based on a communication platform.

In another embodiment, the O-ring seal 122 can have a locator/measuring/signal/sensor device 124 which would identify the longitudinal location of the device 100. Likewise, the device may include a locator/measuring/signal/sensor device along the longitudinal and or radial aspect of the device 100 identifying the longitudinal and radial coordinates of the device 100 such that the physical position can be measured and identified in an integrated network. In this embodiment, each device 100 may include a unique identifier within an individual network. Each device 100 may be connected by remote or direct wiring or a physically attached positioning system.

As best shown in FIG. 2, the distal portion 106 of the percutaneous access device 100 includes one or more accessories 130. For example, an adjustable light source on the distal end 106 would allow a variety of lighting solutions in the operative environment. Accessories 130 can also include an optical imaging device, a camera device, a scope, a video device, a light source, a lighting device, a laser device, a measuring device, a laser measuring device, a signal transmitting device, a signal receiving device, a signal processing device, a memory storage device, a wiring device, a servo driven device, a gear device, an irrigation device, and/or a suction device. A cable 125 extends along the body 102 from the distal end to an external power source (not shown) to provide power to the accessories.

Improved imaging could be obtained by providing a more uniform sourcing of light from variable locations. Alternatively, a variety of imaging devices, measuring devices and energy sources could be used to obtain data necessary to form alternative images, such as three dimensional or holographic images, as compared to images obtained from a single source such as a laparoscope.

Figure 5:
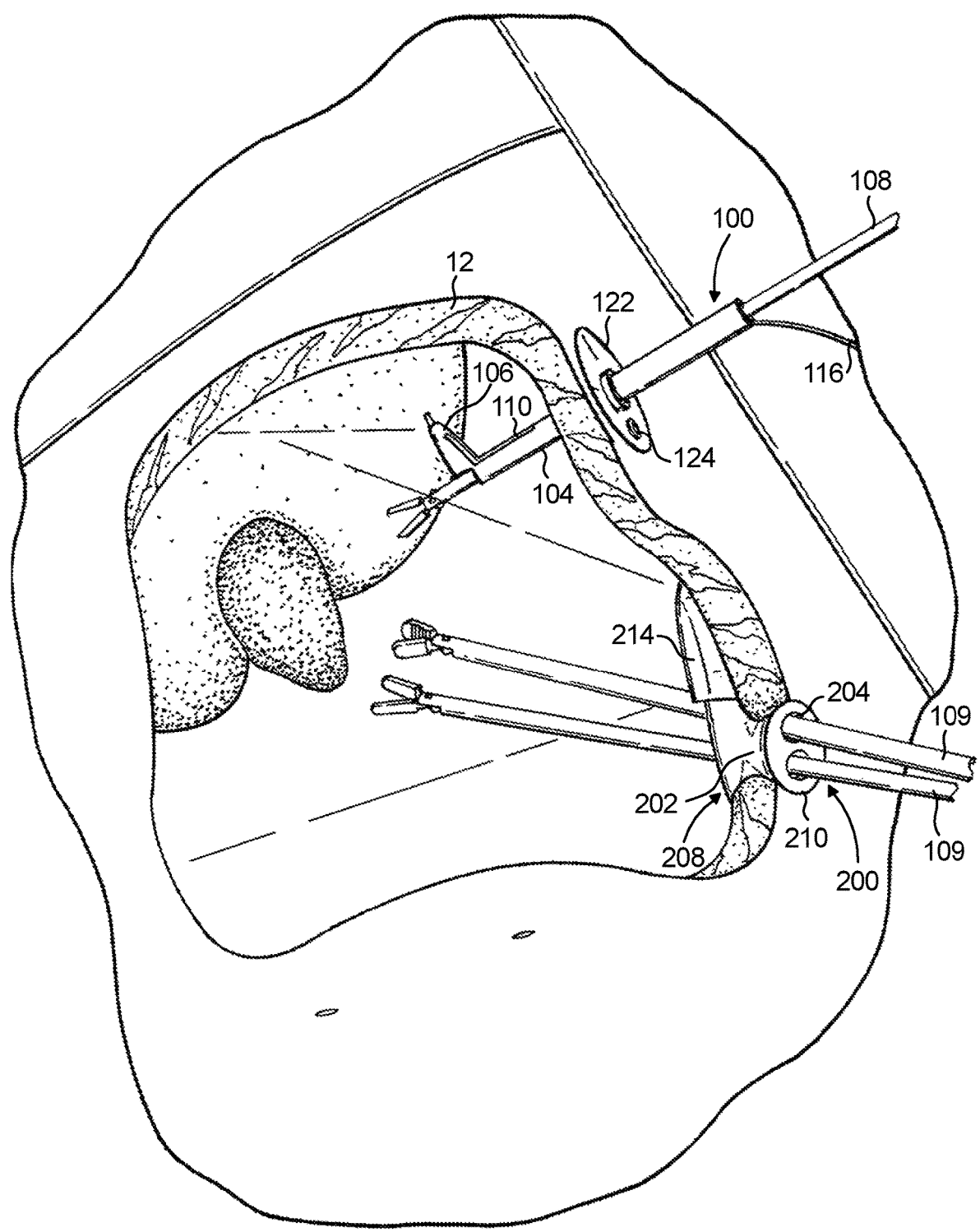
FIG. 5 is a perspective view of a minimally invasive surgical procedure using both the percutaneous access device and access port, being used with at least one surgical instrument inserted through each.
Figure 6:
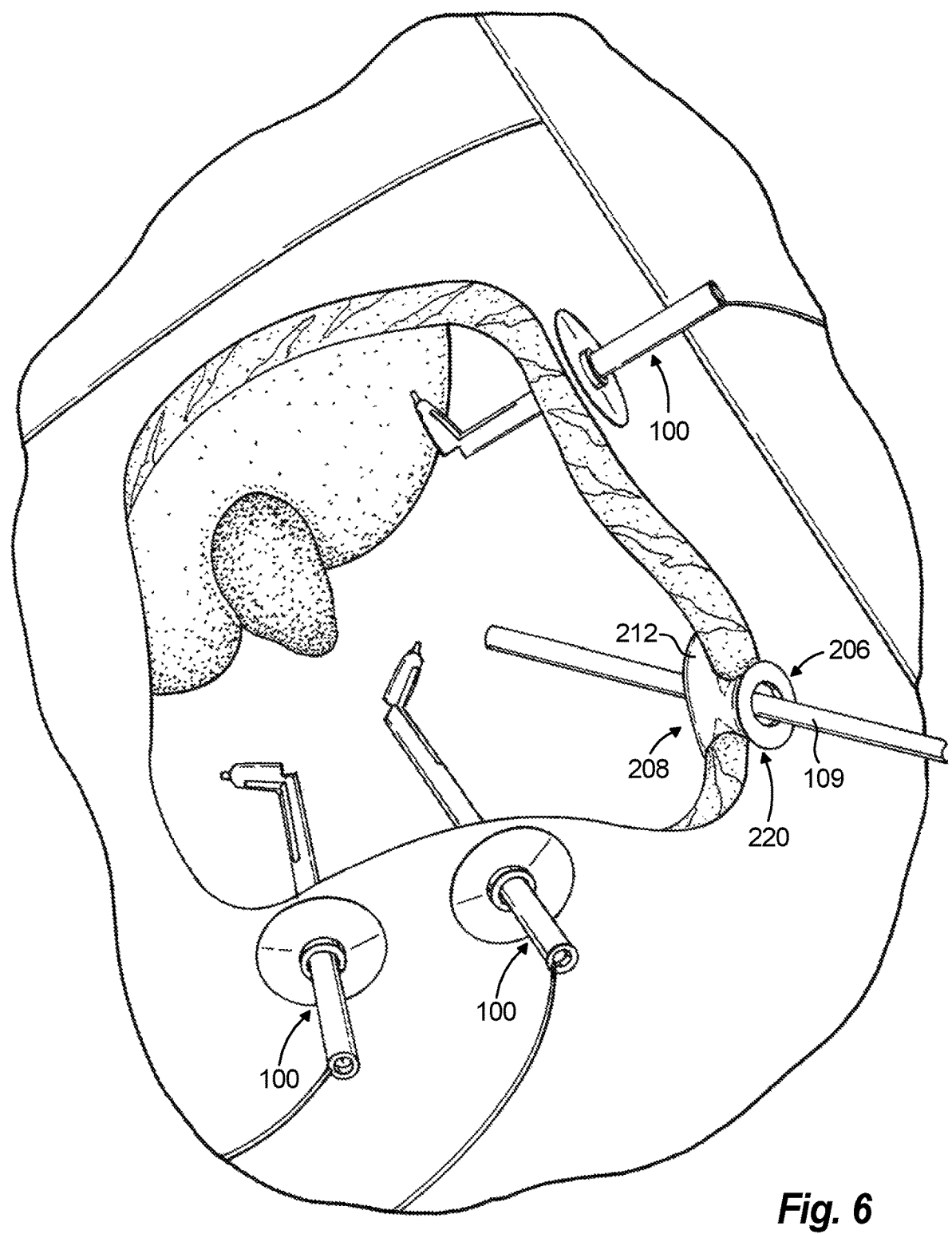
FIG. 6 is a perspective view of another minimally invasive surgical procedure using more than one percutaneous access device along with the access port.
Figure 7:
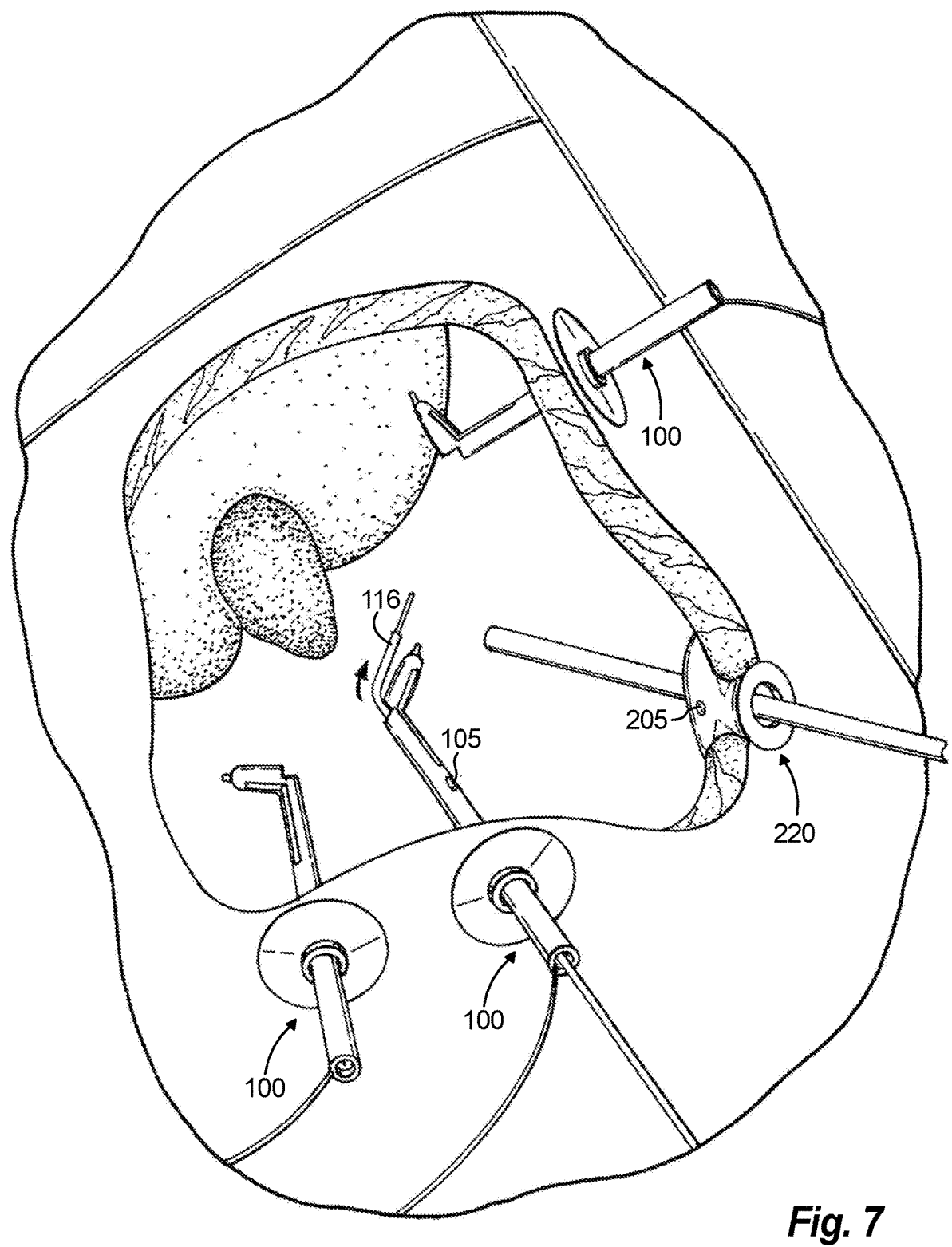
FIG. 7 is a perspective view of the surgical procedure shown in FIG. 6, showing a surgical instrument through at least one of the percutaneous access devices.

With reference now to FIGS. 5-7, the percutaneous access 100 is shown used in conjunction with an access port 200 for a minimally invasive surgical procedure. As illustrated, each incision P1, P2, P3, P4 can accept either an access device 100 or access port 200. It will be understood that the configuration shown is for explanatory purposes and any configuration or number of access devices 100 and access ports 200 can be used without distracting from the scope of the invention.

The access port 200 includes a body 202 defining a bore 204 configured to guide at least one surgical instrument 109 into a patient's abdominal cavity. The access port 200 can include more than one bore 204, as shown in FIG. 5, or the access port 220 can include one bore 204, as shown in FIG. 6. In other embodiments, the access port 300 (shown in FIG. 14) may be a solid structure used for lighting and visual accessories, as will be discussed in further detail below.

Regardless of the number of bores, the body 202 of the access port 200 has a proximal end portion 206 and an opposing distal end portion 208. Several embodiments of the access port are shown and described in further detail in U.S. Patent Publication 2017/0014155 to Norton et al., the disclosure of which is incorporated herein in its entirety.

The proximal end portion 206 includes a first anchoring portion 210 integrally formed with the body 202. The first anchoring portion 210 is generally a concave shape to secure the access port 200 along the abdominal wall 12. The distal end portion 208 includes a second anchoring portion 212 (shown in FIG. 6) which is generally a convex shape projecting radially outwardly from the distal end portion 208 of the body 202 for securing the access port with respect to the interior or the abdominal wall.

As best seen in FIG. 5, the distal end portion 208 can include a light module 214 which can provide an additional lighting source to the interior abdominal cavity. In addition, the light module 214 can provide a location for one or more cameras, and/or measuring and communication devices. With reference to FIGS. 6 and 7, three percutaneous access devices 100 and one access port 200 are inserted into the abdominal wall 12 to work in conjunction on the surgical procedure. FIG. 7 also shows a varying use/embodiment of the guidewire placement/location. In this embodiment, the guidewire 116 can be inserted through the proximal bore 104 and into the abdominal cavity to effect a desired treatment.

Referring now to FIGS. 8-11, an imaging system is coupled to the body of the access port wherein the imaging system can be integrated with a local positioning system and an operative position system to communicate a three dimensional view during a surgical procedure and capture the positioning of the access port 200. The imaging system can include a removable auxiliary module 234 coupled the access port 230 at coupling connector 232 and a plurality of cameras and/or sensors 236 on the distal portion 208 of the access port 230. Preferably, the imaging system can be controlled remotely, manually or by robotics. Cameras 236 of the imaging system may rotate or extend as needed. It is envisioned that the imaging system can also move or include a movable portion which can move either remotely or by robotics.

Figure 10:
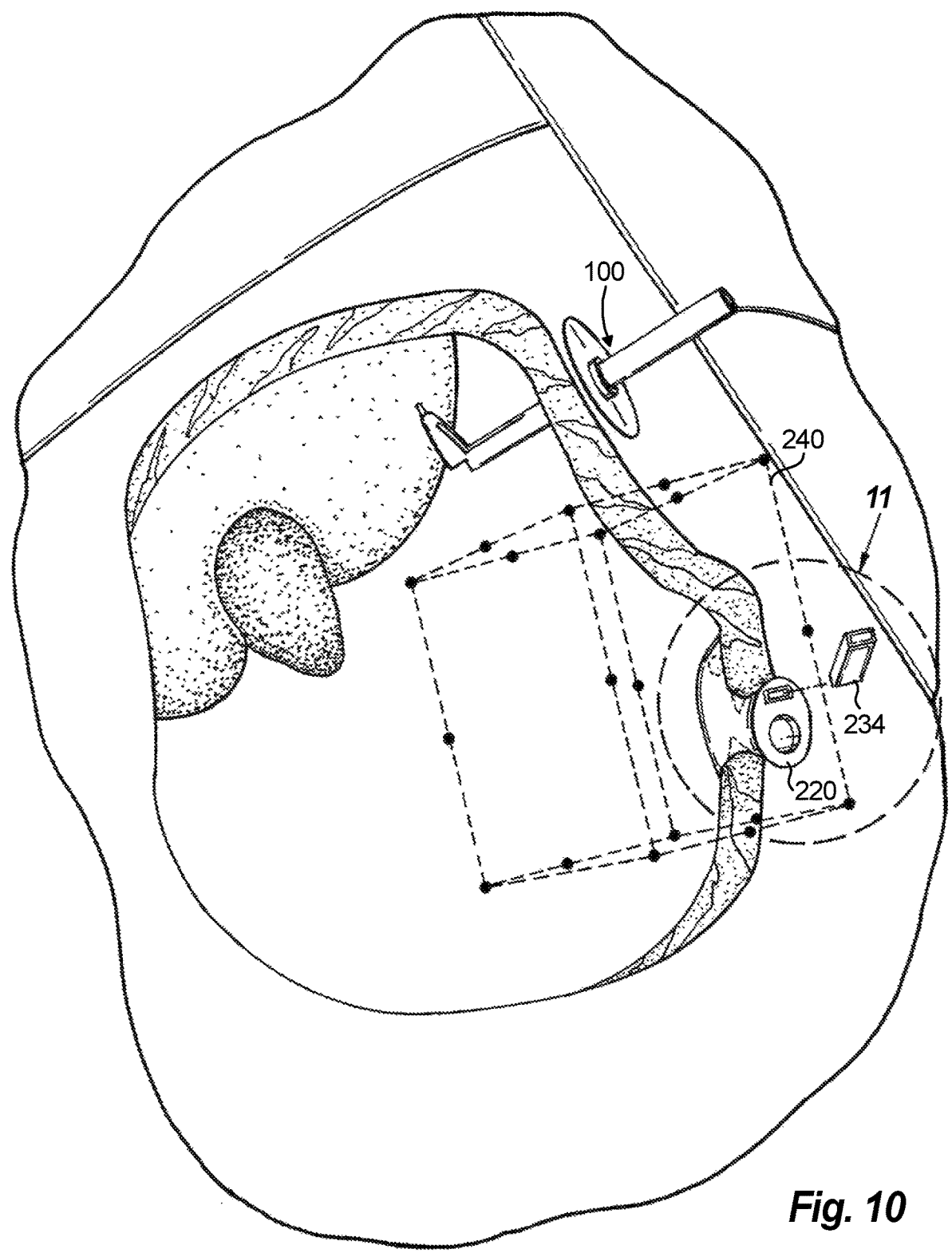
FIG. 10 is a perspective view of the percutaneous access device and the access port during a minimally invasive surgical procedure, showing a three dimensional grid surrounding the access port and a removable auxiliary module.
Figure 11:
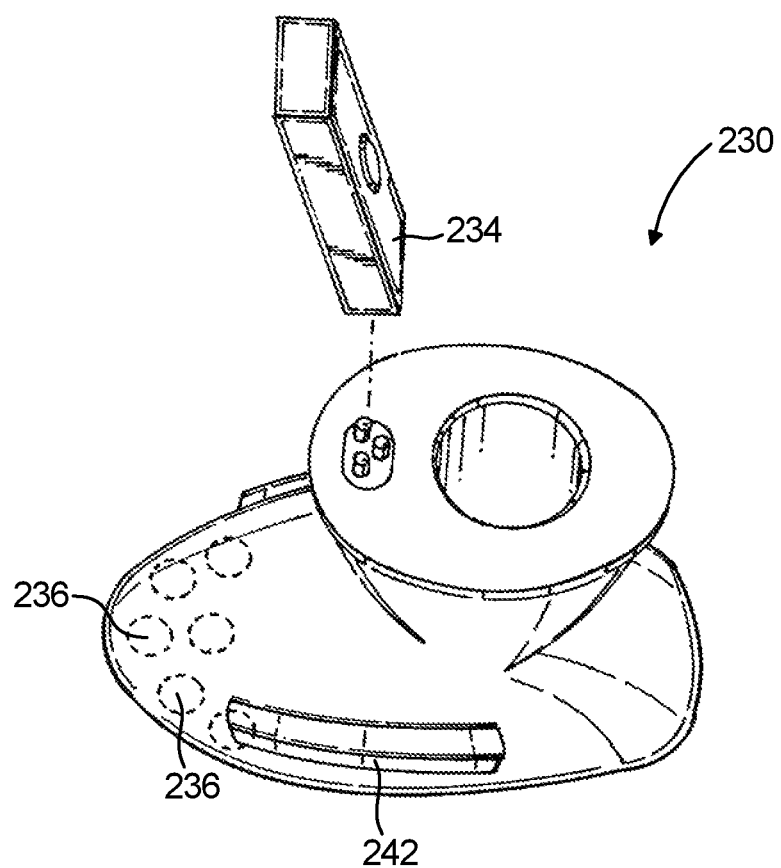
FIG. 11 is a detailed view of the removable auxiliary module of FIG. 10, showing the connection between the module and the access port.

As best seen in FIGS. 10 and 11, the removable auxiliary module 234 provides an expandable platform for the addition of equipment or to arrange the equipment in the most effective use of space. The modular construction of the removable auxiliary module 234 may contain reusable electronics and systems enhancing cost effectiveness. The removable auxiliary module 234 can also contain instruments, mechanical channels, control servos power cables, connectors and computer equipment.

The local positioning system can be a computer related medium, system or program code that captures, integrates and translates a three dimensional grid surrounding the access port 200. The local positioning system can incorporate the views from the imaging system along with data and views from sensors and cameras located in one or more positions in the operating room to achieve a full view of the surgical field. For example, sensor 124 of the seal 122 may be tied into the local position system. In addition, at least one sensor 205 can be located on access port 220 or at least one sensor 105 can be located on the percutaneous access device 100 which can provide positioning information during the surgical procedure. Sensors and imaging devices are shown on the access devices or surgical accessories, however, it will be understood that additional sensors can be located outside the abdominal cavity to provide additional positioning information and view of the operative field.

The operative positioning system communicates the location, position and angle of the access port 200 during the surgical procedure. The operative positioning system consists of measurable points, such as sensor 205 on access port 220. It is envisioned that other measuring points can be placed on the organ of interest or be integrated with laser point measuring originating from the percutaneous access device 100.

With continued reference to FIG. 10 a three dimensional grid 240 is outlined surrounding the access port 220 representing the field of view captured by imaging devices of the imaging system, for example, imaging devices on or within the removable auxiliary module 234 and accessories 236. Views from the imaging devices and the three dimension grid 240 can be translated and viewed on an external monitor to assist the surgeon during the procedure. In other embodiments, the views captured within the grid can be reconstructed into two dimensional, three dimensional images or a holographic image of the operative field.

The operative system allows for the exact position and/or displacement of the access port 200 to be recognized in real-time. For example, unintentional pressure within the abdominal cavity may shift the angle of the access port 200. The operative system can include a notification signal that alerts the surgical team to any and all displacement of the access port 200. A coupling device (not shown) may then be used on edges 242 (shown in FIG. 11) of access port 230 to adjust the displacement of the access port 230 to keep the access port 230 and surgical instrument, for example, 108, therein aligned as needed. The coupling device can be used to adjust and reposition the access port 230 thereby controlling the body of the access port independent of the surgical instrument and functions being performed during the surgical procedure.

The operative system is activated when a surgical instrument is placed through the bore 204 of the access port 200. Ideally, once the operative system is activated the operative system and the local positioning system are engaged and focused on the same focal point. Having both systems focus on single target increases the range of the target.

Figure 8:
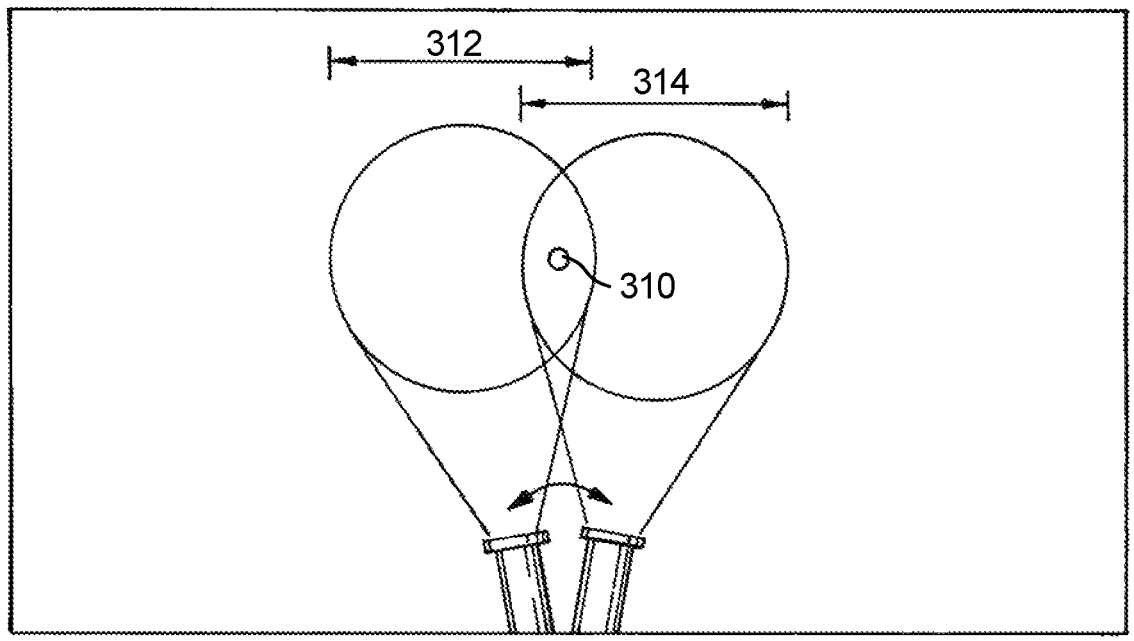
FIG. 8 is schematic illustration showing an engaged system when a local positioning system and operative system are aligned.

As shown in FIG. 8, an engaged system is shown wherein the focal point 310 overlaps the field of view of the access port 312 and the local positioning system 314. An engaged system is analogous to holding one's head and neck in a fixed position and tracking the focal point 310 with one's eye. Having both systems focus on a single target increases the range of view of the target.

Therefore, regardless of any movement or rotation of the imaging devices the focal point 310 remains the same.

Figure 9:
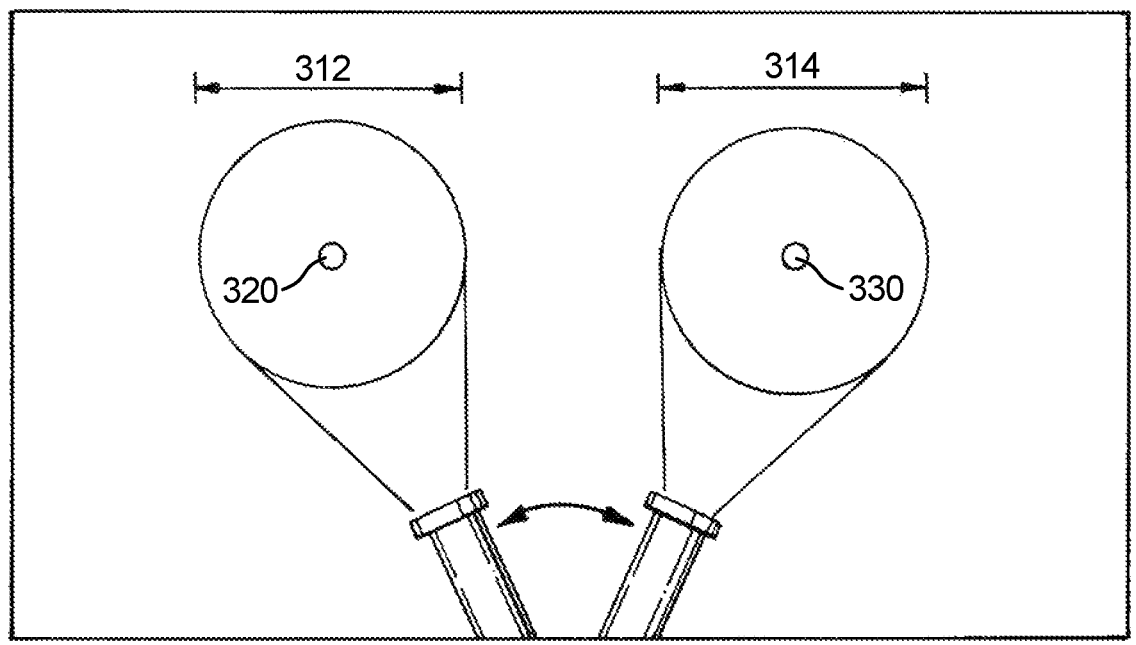
FIG. 9 is schematic illustration showing a disengaged system when the local positioning system and operative system are not aligned.

However, due to the surgical procedure or unintentional movement, the synchronization between the operative system and local positioning system can become disengaged, as shown in FIG. 9. In this scenario the focal point of the access port 312 is now at reference 320 whereas the focal point of the local positioning system is now at 330. A disengaged system is analogous to looking to a new focal point for optical viewing as one moves one's head or neck to reposition one's eyes to look at the chosen focal point. When the systems are disengaged adjustments are needed either to the access port or direction of the imaging and lighting features to reengage the system.

It is envisioned that the imaging system, local positioning system and operative system can be coupled together by direct mechanical connection, direct electrical connection, Bluetooth, Wi-Fi or other electronic communication devices. Integrating the systems with computer graphic systems and robotic systems provides several advantages, for example, auto correction of imaging during motion of the modular imaging device/devices; two dimensional, three dimensional and holographic image reconstruction using computer graphic systems; accurate data for utilization of monocular, binocular, telephoto, and multiple camera image synthesis to guide surgical intervention; and coordination of support systems for retraction, electromechanical surgical instruments, measuring and communication devices for surgery.

Figure 12:
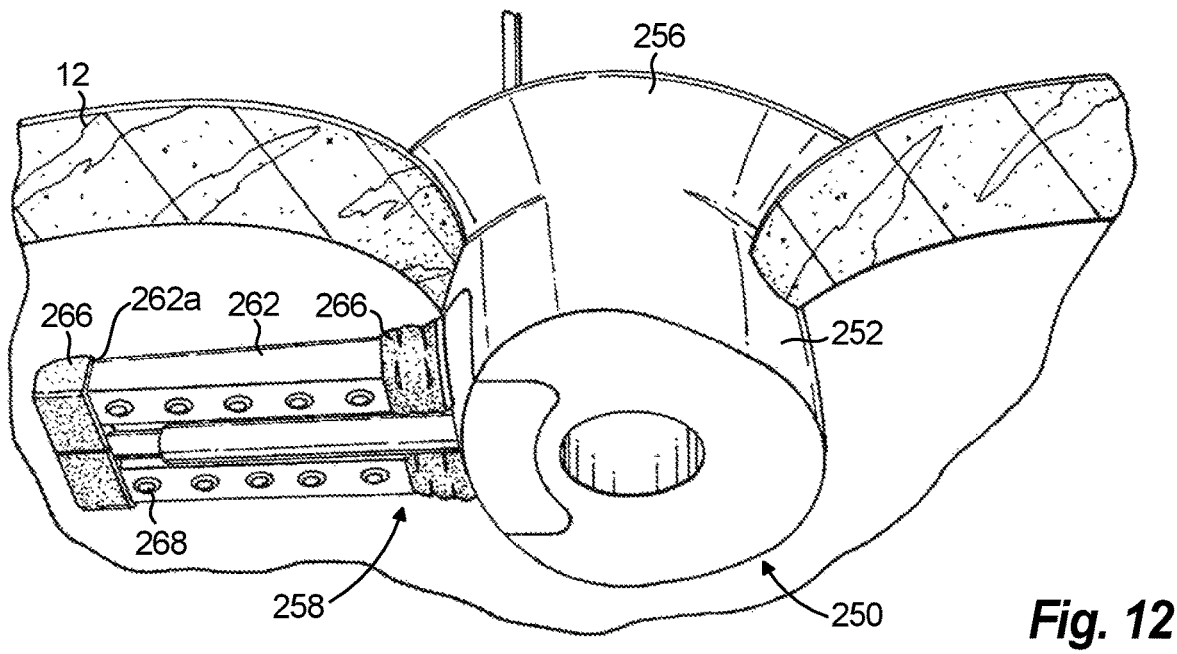
FIG. 12 is a perspective view of an embodiment of an access port with an exemplary multi-segment boot tip in an assembled closed position and oriented for insertion into an incision in the abdominal wall.
Figure 13:
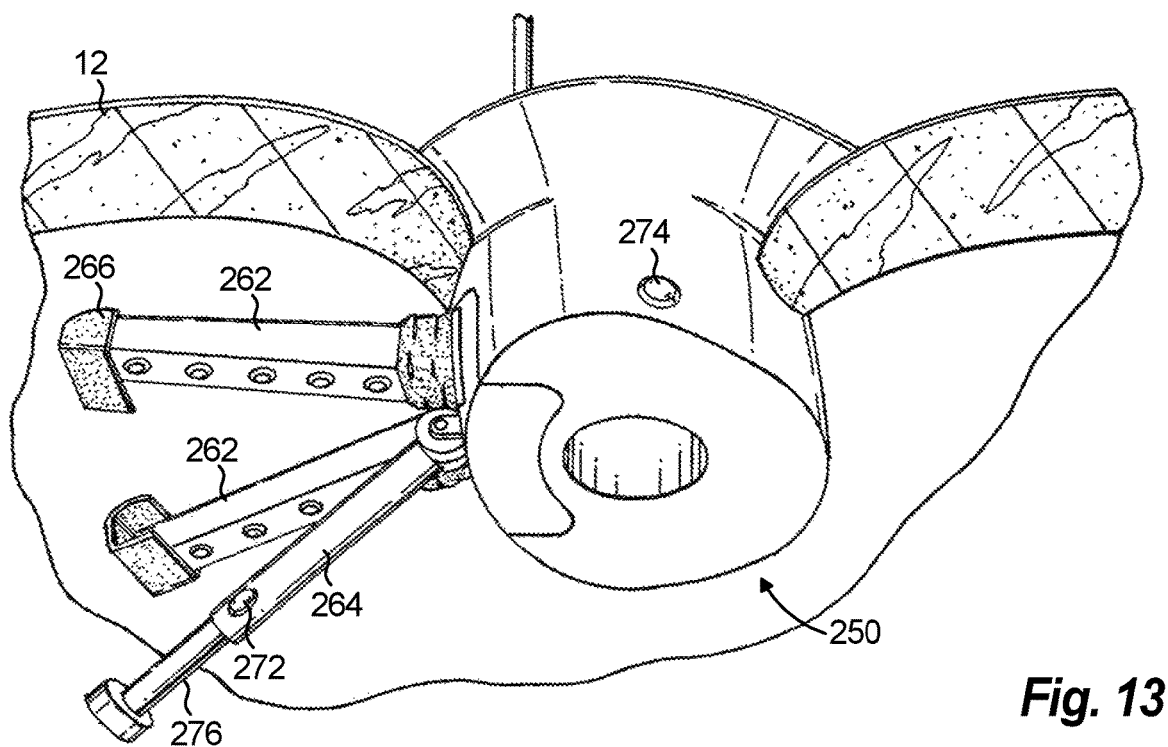
FIG. 13 is a perspective view of the access port and multi-segment boot tip of FIG. 12 in an open position, and installed in the abdominal cavity of a patient.

With reference now to FIGS. 12 and 13, another embodiment of an access port 250 is shown. In this embodiment, the access port 250 includes one bore 254 and first and second anchoring portions 256, 258. The first anchoring portion 256 is integrally formed with the body 252 and is similar in configuration to first anchoring portion 210. The second anchoring portion 258 is an operative platform configured for detachable coupling and articulating movement within the abdominal cavity.

As best seen in FIG. 13, the second anchoring portion 258 can include at least one fixed segment 262 and at least one mobile segment 264. During insertion of the access port 250, the mobile segment 264 may be stowable within the interior volume of the second anchoring portion 258. The fixed segment 262 can include one or more imaging devices and/or lighting devices 268 which can be electronically coupled and remote controlled. The imaging devices 268 may aid in confirming the proper insertion of the access port 250 both during and after insertion. As previously discussed, the imagining and/or lighting devices 268 can be integrated to the local positioning system to give positioning, location, lighting and additional views of the operative site. In addition, a multi-layer monolithically formed transparent shield 266 can be formed along either the fixed or mobile segments 262, 264 to protect the second anchoring portion 258 during and after insertion of the access port 250 within the abdominal cavity. The shield 266 may be integrated or separate or be present in one or more layers. For example, one layer to protect during insertion and/or one layer to protect a camera lens 268 after deployment. The shield 266 may be integrated with a tip 262a of the fixed segment 262. The shield 266 may also be a separate functioning independent accessory.

The shield 266 may be flexible, retractable or dissolvable. In a separate embodiment, the shield 266 may also be bifid allowing for protection of an optical accessory during insertion yet retracted away from the optical accessory during deployment of the access port 250.

The shield 266 may include a single polymer or a plurality laminated polymers or connected layers each of which may be coated separately or in combination with hydrophobic coating to disperse moisture or hydrophilic material to absorb moisture. Micro etching may be utilized to decrease fogging and disperse microscopic and small collections of moisture on the optical shield. These same techniques may be used as a lens protector for a separate integrated or accessory camera attached or inserted with the anchor tip device.

The second anchoring portion 258 may further be temperature adjusted by a separate accessory which may be inserted into the internal space allowing flow of a gas or liquid into the interior space. The purpose is to decrease the moisture deposition on any surface or of the anchor tip itself whither it is interior or exterior. The temperature regulated gas or fluid may be directed to one or more integrated or modular accessory cameras and it may be directed between connected layers of an optical shield to inhibit moisture, moisture collection, fogging and to disperse moisture or fog.

The mobile segment 264 may be in a protective housing or may be adjacent and parallel to the fixed segment 262 during insertion. The mobile segment 264 may have a variety of instruments attached to it which may vary according to the procedure being performed. The instruments may embody similar functional formats or may include a variety of movement mechanisms to position and optimize location for the proposed procedure and instrument function. The mobile segment 264 may carry one or more instruments, lighting, or measuring devices that aid in performing a desired effect of the procedure.

In one embodiment the mobile segment 264 can include an imaging device and be mounted on the distal aspect of a telescoping assembly 276 that is extendable and controllable with an external device by direct control whether it is through direct mechanical, electrical or wireless control. The mobile segment 264 can have the ability to articulate or bend to compliment the requirements of a procedure.

The mobile segment 264 and the body 252 of the access port 250 can each include one or more sensors 272 and 274 which electronically communicate with an external system. For example, sensor 272 of the mobile segment 264 can transfer position information and be electronically coupled to an external control device to move or adjust position as needed. Further, sensors 272, 274 can couple to the local positioning system, described above, to provide additional imaging and location views.

The data received into the local positioning system from the mobile segment 264 may be serially collated as a series of movements and positions needed to accomplish a specific task. The serial collection of data collected can be collated with other measured data and structured in a layered data point matrix from whereby the required articulating instrument position sequence can be derived from the data. Real time instrument positioning collected from one or more instruments or ports can be communicated to a coordinate measuring machine which in turn communicates with the controller of the articulating accessory arm to move to the predicted position as analyzed and communicated by the three dimensional grid.

Figure 14:
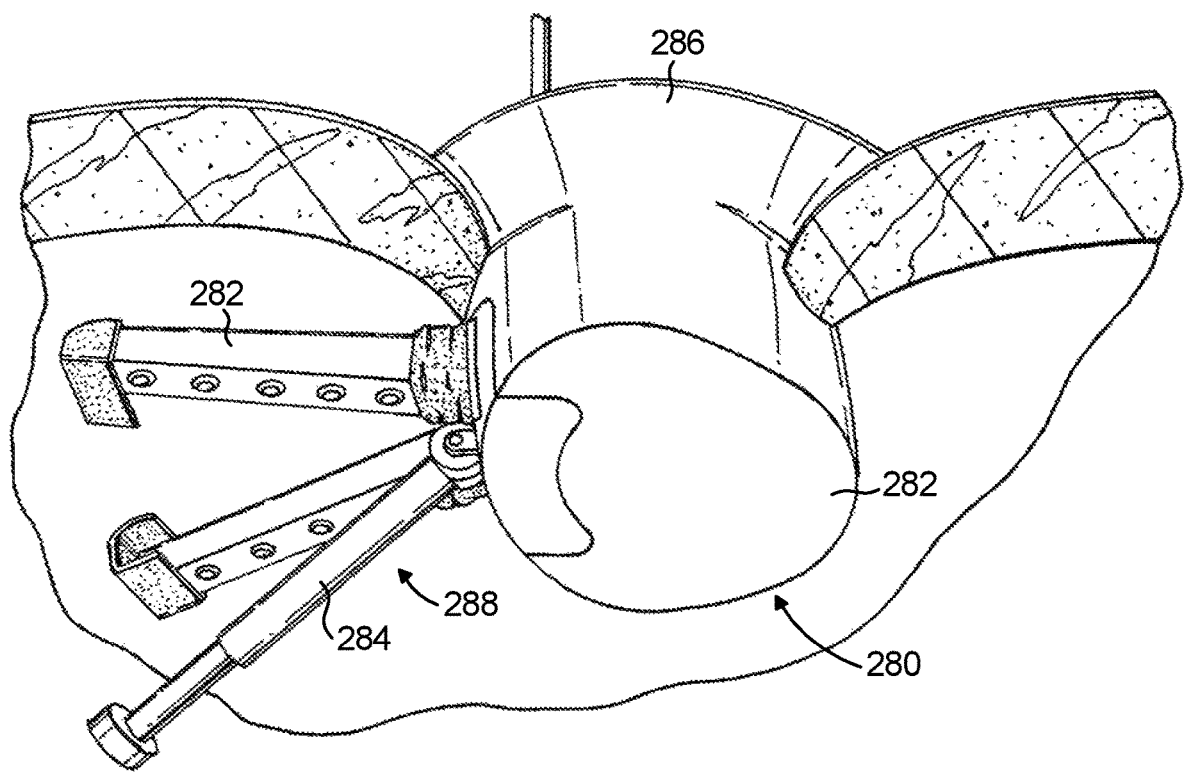
FIG. 14 is a perspective view of another embodiment of the access port and multi-segment boot tip module of the subject invention in an open position wherein a body portion of the access port is a solid structure.

Referring now to FIG. 14, an alternate embodiment of access port 280 is shown wherein the body 282 is a solid device without additional bores. The remaining features of the access port are similar to access port 250 with first and second anchoring portions, 286 and 288. The second anchoring portion including at least one fixed segment 282 and a mobile segment 284.

It will be appreciated that alternative embodiments of modular anchoring devices and the attachment mechanisms between the modular anchoring devices and the bodies of the access devices can be utilized, including, for example, ball and socket joints, mortise and tenon, and male and female pin and receiver. Such joints may be configured in sequence or in parallel as may be required to adapt to particular operative environments. In certain embodiments, one of the boot tip shaped anchoring segments/arms/tips may be fixed in position with one or more additional segments which are mobile such that the fixed segment provides primary support and anchoring to the mobile segments. The mobile segments may attach to the fixed segment, or may be directly attached to the body of the access device. The body of the access device may be provided in other shapes, and is not limited to conical or truncated conical shapes, if different shapes are more effective to meet requirements of a particular operation and operative field. The mobile segments (e.g., mobile arms) can be motorized from within. Alternatively, the fixed segments may function as a primary housing for mechanical and controller devices with the mobile segments functioning in, for example, various of the other capacities listed above. The mobile segments may be controlled by direct control, remote control, first person vision, GPS motion, voice or ocular control, measuring devices, or programmed integrated/coordinated movements.

Alternatively, the primary anchoring segment may be mobile and configured to provide an adjustable (simple or compound) angle, thus providing dynamic positioning adaptable to changing requirements as the operation progresses. The body of the access device may additionally provide workspace housing, equipment mounting, and one or more conduits for wiring, fiberoptics, batteries, lighting, cameras or monitoring sensors in addition to any other devices needed to support the above described components and systems.

It will be appreciated that the embodiments of the inventive disclosure described herein allow for entry into the abdominal cavity through a single access device in a single incision, modularity both inside the access device body (e.g., with detachable seals and inserts which can fluidly couple and fluidly isolate one or more bores of the access device to/from one or more fluid channels defined by the detachable insert), and outside the access device body (e.g., with detachable anchoring portions and sleeves as described herein). The above described embodiments allow the surgeon to spread outward within the abdominal cavity from one or more ports of the access device, in a variable yet controlled manner while supporting surgical accessories adjacent the body of the access device.

While the subject invention has been shown and described with reference to preferred embodiments, those skilled in the art will readily appreciate that various changes and/or modifications may be made thereto without departing from the spirit and scope of the subject invention as defined by the appended claims.

What is claimed is:

1. An access port for use in minimally invasive surgical procedure performed within a patient's abdominal cavity, comprising:
a solid non-perforated body defining a bore, the bore being defined by at least one continuous inner circumference, configured to guide at least one surgical instrument into a patient's abdominal cavity, wherein the solid body has a proximal portion and a distal portion, and wherein the solid body is defined by at least a first continuous outer circumference and a second continuous outer circumference, wherein the first continuous outer circumference is greater than or equal to the second continuous outer circumference;
a first anchoring portion integrally formed with the distal portion of the solid body for anchoring the access port within the patient's abdominal cavity; and
an imaging system coupled to the solid body, wherein the imaging system is integrated with a local positioning system and an operative positioning system to communicate three dimensional positions and views of components utilized during the surgical procedure, wherein the imaging system includes a removable auxiliary module that is coupled to a connector on the proximal portion of the solid body, and which is configured to contain reusable electronics.

2. The access port of claim 1, wherein the distal portion of the solid body includes side edge structures for a coupling device configured to allow the solid body to be controlled independently of other functions performed through the bore or from the auxiliary module.

3. The access port of claim 1, wherein the imaging system includes one or more cameras on the distal portion of the solid body that are remotely controlled, the one or more cameras configured to continuously view a three dimensional grid surrounding the access port.

4. The access port of claim 3, wherein the three dimensional grid viewed by the one or more cameras is translated to create a holographic image of the operative field.

5. The access port of claim 4, wherein the imaging system is activated when a surgical instrument is placed through the bore in the solid body of the access port.

6. The access port of claim 3, wherein the imaging system further includes imaging devices and position sensors located in one or more positions in an operating room.

7. The access port of claim 3, wherein the three dimensional grid is configured to be recorded into a central data storage supporting artificial intelligence to produce independent camera movement based on position sensor utilization positions and the corresponding camera position.

8. The access port as recited in claim 1, wherein the removable module is configured to contain instruments, mechanical channels, control servos, power cables, connectors and computer equipment.

9. An access port for use in minimally invasive surgical procedure performed within a patient's abdominal cavity, comprising:
a solid non-perforated body defining a bore, the bore being defined by at least one continuous inner circumference, configured to guide at least one surgical instrument into a patient's abdominal cavity, and having a distal portion and a proximal portion, the distal portion of the solid body including an anchoring portion to secure the access port with respect to a wall of the abdominal cavity, wherein the solid body is defined by at least a first continuous outer circumference and a second continuous outer circumference, wherein the first continuous outer circumference is greater than or equal to the second continuous outer circumference; and
an imaging system including a removable module coupled to a connector on the proximal portion of the solid body and a plurality of cameras on the distal portion of the solid body, the removable module including means to communicate three dimensional views of the surgical procedure from the cameras to an external monitor.

10. The access port as recited in claim 9, wherein the distal portion of the solid body includes first and second anchoring portions, and wherein the second anchoring portion includes at least one fixed segment and a mobile segment.

11. The access port as recited in claim 9, wherein the anchoring portion includes side edge structures for enabling a device to adjust and reposition the access port.

12. The access port as recited in claim 9, wherein the removable module is configured to contain reusable electronics.

13. The access port as recited in claim 9, wherein the removable module is configured to contain instruments, mechanical channels, control servos, power cables, connectors and computer equipment.

* * * * *